United States Patent [19]
Watson et al.

[11] Patent Number: 5,738,641
[45] Date of Patent: Apr. 14, 1998

[54] BLOOD WITHDRAWAL PATCH

[76] Inventors: Robert L. Watson, 1704 Singletree Way, Bowling Green, Ky. 42103; William R. Knepshield, 889 S. Matlack St., West Chester, Pa. 19382

[21] Appl. No.: 688,845

[22] Filed: Jul. 31, 1996

[51] Int. Cl.⁶ ...................................... A61F 13/00
[52] U.S. Cl. ................... 602/43; 602/54; 604/180
[58] Field of Search ........................... 604/116, 174, 604/180; 128/DIG. 26, 760; 602/41–43, 52, 54, 57

[56] References Cited

U.S. PATENT DOCUMENTS

| | | | |
|---|---|---|---|
| 4,978,342 | 12/1990 | Heimreid | 604/180 |
| 5,254,095 | 10/1993 | Harvey | 604/115 |
| 5,447,492 | 9/1995 | Cartmell et al. | 602/58 |
| 5,496,264 | 3/1996 | Watson et al. | 604/28 |
| 5,569,223 | 10/1996 | Wandell et al. | 604/290 |

*Primary Examiner*—Corrine M. McDermott
*Attorney, Agent, or Firm*—Walter C. Farley

[57] ABSTRACT

A blood withdrawal patch for facilitating withdrawal from a patient and for confining blood from the needle wound has an absorbent pad with a first surface to be placed against the skin of a patient around an intended injection site, a second surface opposite the first surface and a central opening. A transparent, elastomeric, self-sealing membrane through which an injection needle can penetrate lies in the pad central opening. A transparent cover layer has a central opening substantially aligned with the central opening of the pad to expose a central portion of the membrane to identify the withdrawal site, the cover layer being adhered to the membrane and the pad. The patch is adhesively held on the patient's skin. A blood vessel is visually located through the membrane and cover and a needle is passed through the membrane and the patient's skin into the vessel for blood withdrawal. After withdrawal, the needle is extracted, and the membrane wipes the needle and forms a cavity with the pad and the patient's skin to contain blood from the withdrawal site until after hemostasis. The patch is also useful for installation of a catheter.

9 Claims, 3 Drawing Sheets

Fig. 5
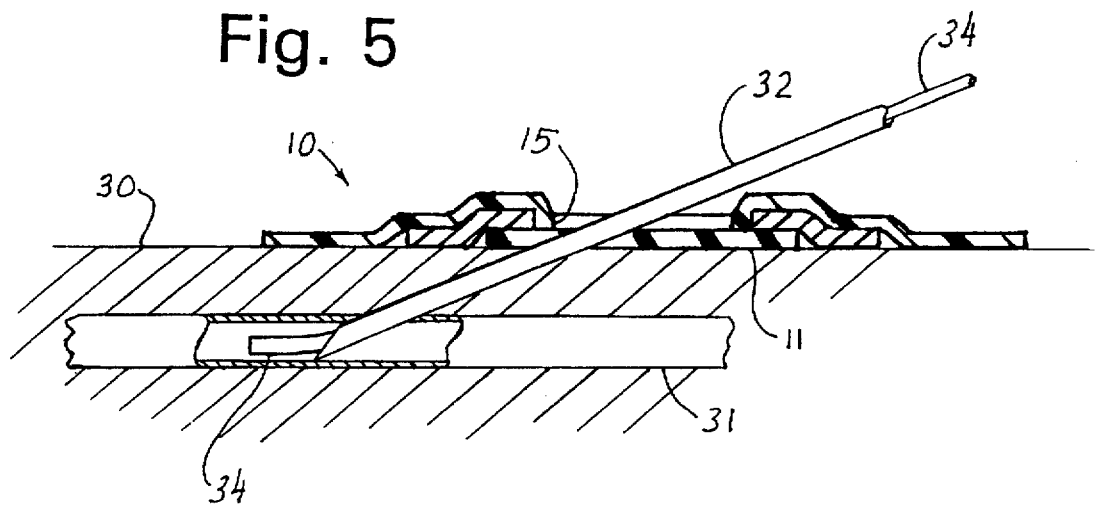
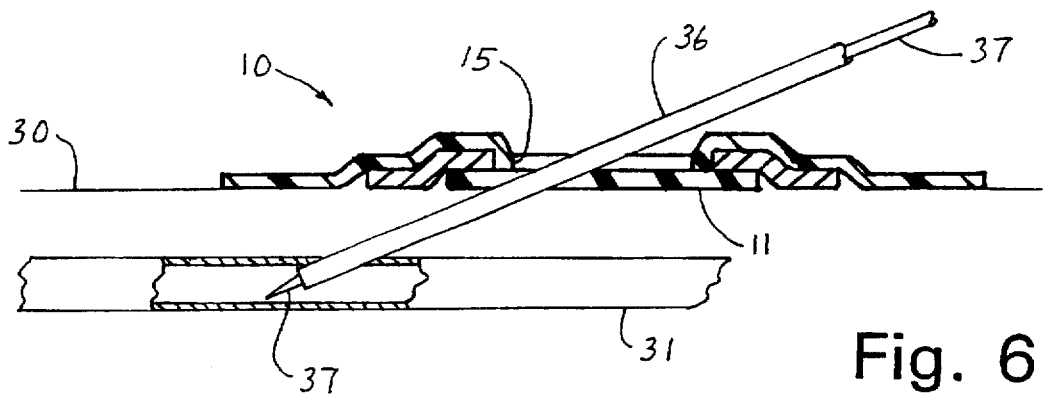
Fig. 6

BLOOD WITHDRAWAL PATCH

FIELD OF THE INVENTION

This invention relates to an adhesive patch through which blood can be withdrawn from a patient for minimizing health care worker contact with the blood of the patient.

BACKGROUND OF THE INVENTION

In recent years, it has been officially and widely recognized that blood-borne pathogens are an important and serious method of transmission of infectious diseases. Health care workers in particular are in danger from such exposure, but the danger exists for any person who is likely to come in contact with the blood of a person who is infected with such a disease.

Commonly, when an injection is being made, the target area of the patient's skin is wiped with a disinfectant and the injection is made through the skin subcutaneously or intramuscularly using a needle and syringe. After the injection has been made, the needle is withdrawn and a pad of gauze or cotton is placed on the puncture wound to absorb any blood which may emanate therefrom. The pad may be left in place or temporarily taped to the wound. In this typical scenario, not only is the health care worker giving the injection in danger of exposure to the patient's blood but so also is any other health care worker or other person who might come in contact with the area of the puncture wound.

The Occupational Safety and Health Administration (OSHA), the Food and Drug Administration (FDA), and the Center for Disease Control (CDC) have recommended that all human blood and other potentially infectious materials be treated as if known to be infectious for HIV, HBV or other blood-borne pathogens regardless of the perceived low risk of a patient or patient population. However, no effective means for meeting this recommended standard has existed.

SUMMARY OF THE INVENTION

An object of the present invention is to provide a patch through which fluid such as blood can be withdrawn and which, after withdrawal, contains blood under a sterile, self-sealing, non-coring, non-latex elastomeric membrane.

Another object is to provide such a patch which includes an adhesive absorptive circumferential pad for absorbing any blood coming in contact with it and containing the blood under the membrane.

A further object is to provide as part of the patch a seal to be adhered to the outer surface of the patch to contain any blood which may be left on the outer surface thereof from the extracted needle.

Briefly described, the invention comprises a blood withdrawal patch for facilitating withdrawal from a patient and for confining blood from the needle wound including an absorbent pad having a first surface to be placed against the skin of a patient around an intended injection site, a second surface opposite the first surface and a central opening. A transparent, elastomeric, self-sealing membrane through which an injection needle can penetrate lies against the second surface of the pad in its central opening. A transparent cover layer has a central opening substantially aligned with the central opening of the pad to expose a central portion of the membrane to identify the withdrawal site, the cover layer being adhered to the membrane and the pad. The patch is adhesively held on the patient's skin, whereby a blood vessel can be located through the membrane and cover and a needle can be passed through said membrane and the patient's skin into the vessel for blood withdrawal. After withdrawal, the needle is extracted, and the membrane wipes the needle and forms a cavity with the pad and the patient's skin to contain blood from the withdrawal site until after hemostasis.

BRIEF DESCRIPTION OF THE DRAWINGS

In order to impart full understanding of the manner in which these and other objects are attained in accordance with the invention, particularly advantageous embodiments thereof will be described with reference to the following drawings, which form a part of this disclosure, and wherein:

FIG. 5 is a schematic side elevation, in section, of the patch of FIGS. 1–4 applied to the skin of a patient for use in inserting a catheter from within a needle; and FIG. 6 is a schematic side elevation, in section, of the patch of FIGS. 1–4 applied to the skin of a patient for use in inserting a catheter from outside of a needle.

DESCRIPTION OF THE PREFERRED EMBODIMENTS

Figure 1:
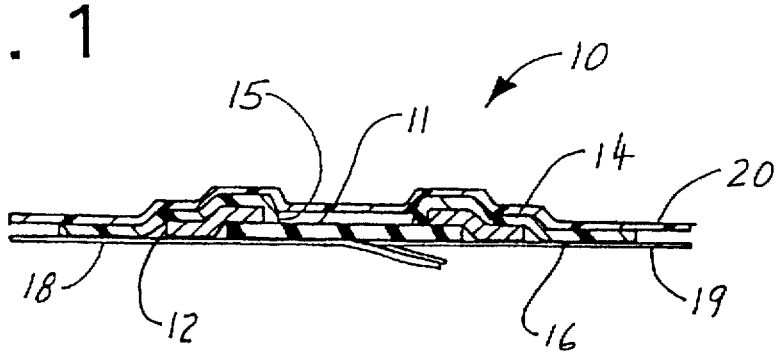
FIG. 1 is a schematic side elevation, in section along line 1—1 of FIG. 2, of a patch in accordance with the invention.

Before discussing the structure of the invention in detail, it will be noted that the layers of material used in the structure are quite thin. In the various figures, the thicknesses are exaggerated for clarity of illustration and it will be realized that this exaggeration also exaggerates the curvatures which occur in the drawings at the overlapping intersections of various layers.

Figure 2:
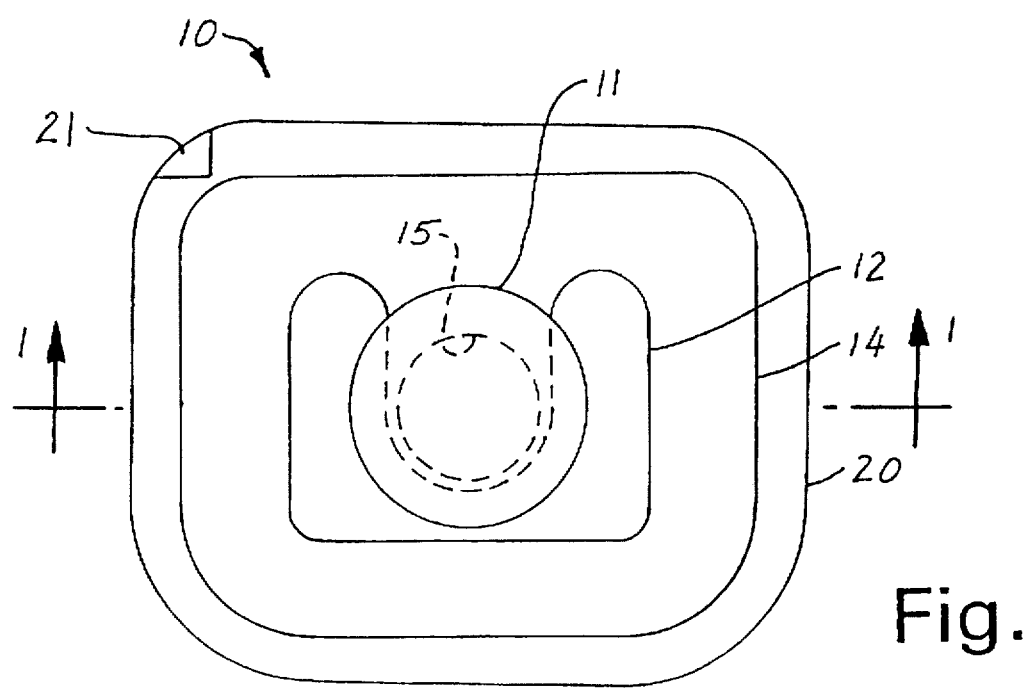
FIG. 2 is a bottom plan view of the patch of FIG. 1 with the release-paper butterfly removed therefrom to expose other components.

FIGS. 1 and 2 show a blood withdrawal patch indicated generally at 10 in accordance with the invention which includes a sterile, self-sealing, non-coring, non-latex and transparent elastomeric membrane 11. In the embodiment shown, membrane 11 is circular, although other shapes can be used. A generally C-shaped absorbent pad 12 lies around and partially on membrane 11. A cover 14 lies over pad 12 and membrane 11, cover 14 having a central opening 15 substantially centrally aligned with the membrane and an adhesive inner surface 16 facing the pad and membrane. Thus, cover 14 holds the pad and membrane together and to itself, and also provides a large marginal adhesive area by which the patch is attached to the skin of a patient. Until the patch is about to be used, the exposed adhesive portions of cover 14 are covered by a sterile butterfly including sheets 18 and 19 of a conventional release paper which can be readily removed from the adhesive cover. It will be noticed that the overlap of butterfly sheets 18 and 19 is offset from the center of membrane 11 to permit a health care worker to see through the patch as it is applied, as will be described.

The outer surface of cover 14 is kept sterile by a thin, removable sheet 20 which is lightly adhered to the cover, i.e., sheet 20 is much less strongly adhered to cover 14 than cover 14 is to a patient's skin. A corner of cover 20 is provided with a non-adhesive marker 21 which can be grasped easily to facilitate removal of the cover.

Figure 3:
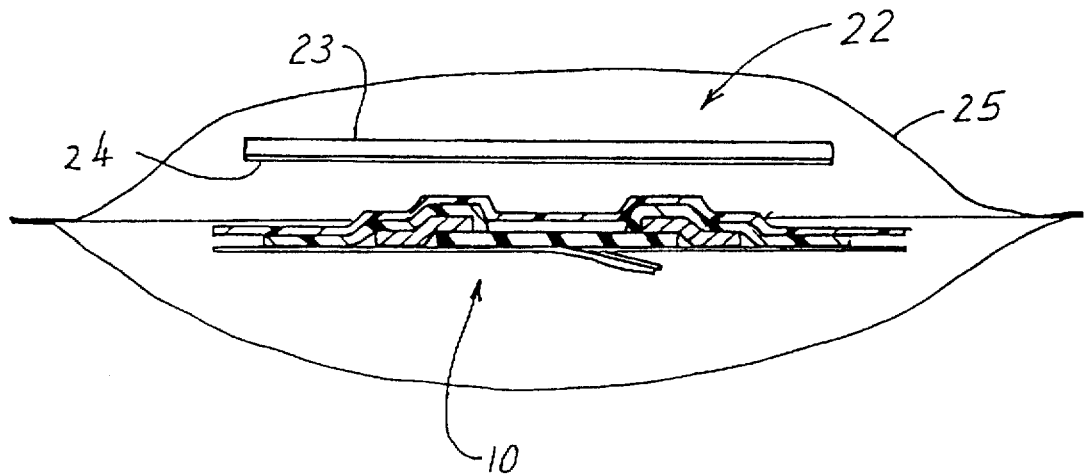
FIG. 3 is a schematic sectional side elevation of a patch in accordance with the invention as provided in a sterile package.

An additional component of the patch is an adhesive seal 22 which is supplied with patch 10 in a package 25 having a sterile interior, the package and contents being schematically shown in FIG. 3. Seal 22 comprises a rectangular pad 23 of an opaque, elastic foam material having an adhesive-coated surface which, until use, is covered by a conventional release paper sheet 24. As will be described, pad 23 is used to cover the membrane after blood withdrawal.

It is important to note that membrane 11, cover 14 and removable sheet 20 must be substantially transparent, i.e., sufficiently optically clear so that the health care worker can see a vein or artery through these components as the patch is being positioned on the patient. It is also important that the butterfly separation be laterally offset so that when one side of the butterfly is removed, the other side of the butterfly does not obscure the health care workers vision through the membrane. The specific reasons for this will become more understandable from the following description of how the patch is applied and used, taking withdrawal from the arm of a patient as an example. As will be recognized, the patch is applicable to blood withdrawal from a vein or artery, as in arterial bloodgas withdrawal.

The area of the skin adjacent the intended blood withdrawal site, vein or artery, is aseptically prepared by either an ethanol or betadine thorough wipe. In the case of a venous withdrawal, a tourniquet is applied in the usual manner to the arm proximal to the vena puncture site.

Package 25 is opened and patch 10 and seal 22 are removed. Patch 10 is oriented so that the open end of C-shaped absorptive pad 12 is directed toward the proximal part of the patient's arm. The first side 18 of the butterfly backing is removed with the health care worker's left thumb and index finger, pulling the backing from right to left and exposing the center elastomeric membrane which is then positioned over the withdrawal site. The membrane is pressed against the site as the butterfly backing is removed so that the membrane and the adhesive surface of cover 14 adhere to the skin. The second butterfly backing 19 is grasped by the right thumb and index finger and is removed from left to right while pressing the sterile adhesive surface 16 to the skin.

Figure 4:
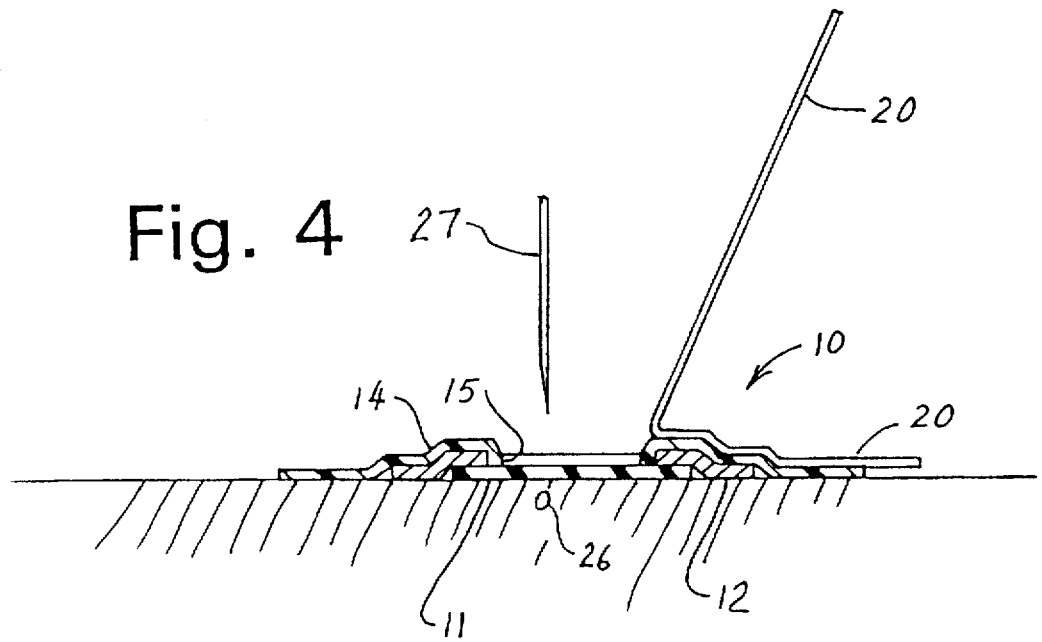
FIG. 4 is a schematic side elevation, in section, of the patch of FIGS. 1 and 2 applied to the skin of a patient.

With the patch adhered to the skin as seen in FIG. 4, cover sheet 20 is removed by grasping marker 21 at the free corner thereof with the right thumb and index finger and pulling left to right, exposing the sterile outer surface of cover 14 and, through central opening 15, the outer surface of the membrane.

Following the above application of the sterile patch to the patient's skin, venipuncture or arterial bloodgas withdrawal is performed in the usual manner, passing a withdrawal needle 27 through non-coring, self-sealing membrane 11 into the selected blood vessel 26.

After blood withdrawal, the needle is extracted from the patient and from the membrane and appropriately discarded. Normally the blood is collected in a previously evacuated vial or the like, not shown, which accepts all blood removed from the patient. During extraction of the needle, the membrane essentially wipes clean the outer surface of the needle and contains all bleeding from the patient's puncture wound within a cavity formed by the membrane, the absorptive pad and the adhesive cover. However, it is possible, and not unusual, for a minute quantity of blood from the interior of the extracted needle to be left on the outer surface of the membrane. Also, because the membrane is transparent, it is possible to see blood which has escaped from the puncture wound. To seal this exposed blood, if any, and obscure the visible blood under the membrane, pad 23 is removed from the release paper 24 of the separate seal and is applied to the outer surface of the membrane and cover.

Pressure may be applied to pad 24. Following an arterial puncture for a blood gas laboratory withdrawal, pressure is mandatory for the usual 5 minute protocol standard. The patch should not be removed for 10 minutes, or until hemostasis has occurred, and not until a proper pad disposal container is available. Additionally, the patch creates it own pressure, to a small but effective degree, as blood enters the chamber described above between the skin and the membrane, aiding in reducing further bleeding and promoting hemostasis.

As will be recognized from the above, proper use of the patch described herein absolutely contains post blood withdrawal bleeding to the patient and under a sterile pad until hemostasis has occurred, thereby hygienically limiting exposure of the blood to others.

A patch in accordance with the invention is also useful to insert a catheter into a patient. While such catheters and their insertion is known, the patch greatly improves the safety of insertion and assists in securely holding the catheter in position after insertion and the removal of the needle has been completed.

One example of this is shown, somewhat enlarged and not to scale, in FIG. 5 wherein a patch 10 is applied to the skin 30 of a patient. A needle 32 is passed through opening 15 and penetrates membrane 11, passing through the skin and subcutaneous tissue to enter a fluid vessel within the body. Needle 32 contains a small catheter 34, typically made of Teflon® or the like, which is passed into the vessel. The needle is then removed in a conventional fashion, leaving the catheter in place.

When the needle is removed, membrane 11 not only closes the opening formed by the needle, thereby containing any body fluids which might tend to escape from the puncture wound, but also tightly seals around the catheter, snugly holding the catheter in place for administration of medication or the like. As will be recognized, this technique is one which is commonly used for withdrawing or inserting fluids out of or into the spinal cord. Use of the patch greatly facilitates this technique. After removal of the catheter, a cover 23 is applied to the patch as described above.

FIG. 6 shows an alternative technique using a catheter 36 which is external of a needle 37. The technique is basically similar and need not be described again in detail.

While certain advantageous embodiments have been chosen to illustrate the invention, it will be understood by those skilled in the art that various modifications can be made therein without departing from the scope of the invention as defined in the appended claims.

What is claimed is:

1. A patch for facilitating injection into or withdrawal of blood from a patient and for confining blood from the needle wound comprising an absorbent pad having a first surface to be placed against the skin of a patient around an intended penetration site for injection or withdrawal and a central opening;

a transparent, elastomeric, self-sealing membrane through which a needle can penetrate; and a transparent cover layer having an outer surface and an adhesive surface for holding said membrane in said central opening of said pad and for adhering said patch to skin of a patient, and having a central opening substantially aligned with the central opening of said pad to expose a central portion of the membrane allowing visual identification of a selected penetration site whereby a blood vessel can be located through the membrane and cover and a needle can be passed through said membrane and the patient's skin into a vessel for injection or blood withdrawal, and whereby, after injection or withdrawal, the needle is extracted, the membrane wipes the needle and forms a cavity with the pad and the patient's skin to contain blood from the penetration site until after hemostasis.

2. The patch according to claim 1 and further comprising first and second release paper covers for covering said adhesive surface of said cover layer until the patch is ready for use, said release paper covers overlapping at a location laterally offset from said membrane to permit visual positioning of said patch through said membrane after removal of one of said release paper covers as said patch is applied to the patient's skin.

3. The patch according to claim 2 and further comprising a seal comprising an opaque pad having an adhesive surface for covering said membrane after extraction of the needle therefrom.

4. The patch according to claim 3 and further comprising an outer cover lightly adhered to said outer surface of said cover layer for maintaining sterility of said outer surface until after said patch is applied to skin of a patient.

5. The patch according to claim 4 wherein said pad is generally C-shaped around said central opening.

6. The patch according to claim 1 and further comprising a seal comprising an opaque pad having an adhesive surface for covering said membrane after extraction of the needle therefrom.

7. The patch according to claim 1 and further comprising an outer cover lightly adhered to said outer surface of said cover layer for maintaining sterility of said outer surface until after said patch is applied to skin of a patient.

8. A patch for facilitating installation of a catheter in a patient with a needle and for confining body fluid from the needle wound comprising an absorbent pad having a first surface to be placed against the skin of a patient around an intended puncture site and a central opening;

a transparent, elastomeric, self-sealing membrane through which a needle can penetrate; and a transparent cover layer having an outer surface and an adhesive surface for holding said membrane in said central opening of said pad and for adhering said patch to skin of a patient, and having a central opening substantially aligned with the central opening of said pad to expose a central portion of the membrane allowing visual identification of the selected puncture site whereby a selected body part can be located through the membrane and cover and a needle can be passed through said membrane and the patient's skin into the body part for catheter installation and whereby, after installation, the needle is extracted, the membrane wipes the needle and forms a seal with the catheter and a cavity with the pad and the patient's skin to contain body fluid from the puncture site.

9. A fluid injection or withdrawal product comprising an envelope with a sterile interior;

a first patch in said envelope comprising an absorbent pad having a first surface to be placed against the skin of a patient around an intended penetration site and a central opening;

a transparent, elastomeric, self-sealing membrane through which an injection or withdrawal needle can penetrate; and a transparent cover layer having an outer surface and an adhesive surface for holding said membrane in said central opening of said pad and for adhering said patch to skin of a patient, and having a central opening substantially aligned with the central opening of said pad to expose a central portion of the membrane allowing visual identification of a selected penetration site whereby a blood vessel can be located through the membrane and cover and a needle can be passed through said membrane and the patient's skin into a vessel for injection or blood withdrawal, and whereby, after injection or withdrawal, the needle is extracted, the membrane wipes the needle and forms a cavity with the pad and the patient's skin to contain blood from the penetration site until after hemostasis; and a seal in said envelope, said seal comprising an opaque pad having an adhesive surface for covering said membrane after extraction of the needle therefrom.

* * * * *